(12) United States Patent
Ferrito et al.

(10) Patent No.: US 10,011,687 B2
(45) Date of Patent: Jul. 3, 2018

(54) HYDROPHILIC ORGANOSILANES

(71) Applicants: Dow Silicones Corporation, Midland, MI (US); Dow Corning Toray Co., Ltd., Tokyo (JP); Dow Corning (China) Holding Co., Ltd, Shanghai (CN)

(72) Inventors: Michael Ferrito, Midland, MI (US); Michal Hrebicik, Benesov Prahy (CZ); Scott Miller, Freeland, MI (US); Lenin James Petroff, Bay City, MI (US); Guodong Robin Shen, Shanghai (CN); Gerald Witucki, Midland, MI (US); Takeshi Yoshizawa, Chiba (JP)

(73) Assignees: Dow Silicones Corporation, Midland, MI (US); Dow Corning Toray Co., Ltd., Tokyo (JP); Dow Corning (China) Holding Co., Ltd, Shanghai (CN)

( * ) Notice: Subject to any disclaimer, the term of this patent is extended or adjusted under 35 U.S.C. 154(b) by 0 days.

(21) Appl. No.: 14/889,704

(22) PCT Filed: May 7, 2014

(86) PCT No.: PCT/US2014/037175
§ 371 (c)(1),
(2) Date: Nov. 6, 2015

(87) PCT Pub. No.: WO2014/182830
PCT Pub. Date: Nov. 13, 2014

(65) Prior Publication Data
US 2016/0122478 A1 May 5, 2016

(30) Foreign Application Priority Data

May 8, 2013 (CN) ................. PCT/CN2013/075345
May 8, 2013 (PL) ..................................... P.403810

(51) Int. Cl.
| | |
|---|---|
| *C07F 7/18* | (2006.01) |
| *C08K 5/5419* | (2006.01) |
| *C08G 81/00* | (2006.01) |
| *C08B 15/05* | (2006.01) |
| *C08G 65/336* | (2006.01) |
| *C09D 5/00* | (2006.01) |

(52) U.S. Cl.
CPC ............. *C08G 81/00* (2013.01); *C07F 7/184* (2013.01); *C07F 7/1876* (2013.01); *C08B 15/05* (2013.01); *C08G 65/336* (2013.01); *C08K 5/5419* (2013.01); *C09D 5/00* (2013.01)

(58) Field of Classification Search
CPC ........ C07F 7/184; C07F 7/1844; C07F 7/182; C08K 5/5419
See application file for complete search history.

(56) References Cited

U.S. PATENT DOCUMENTS

| | | | | |
|---|---|---|---|---|
| 4,207,071 A | * | 6/1980 | Lipowitz ............ | D06M 13/513 427/387 |
| 5,430,166 A | * | 7/1995 | Klein .................. | B01F 17/0071 516/199 |
| 5,707,550 A | * | 1/1998 | Glover ................... | A61K 8/585 424/70.19 |
| 6,228,968 B1 | * | 5/2001 | Yoshioka ............... | A61K 8/893 424/401 |
| 2006/0160935 A1 | * | 7/2006 | Hasse ...................... | C08K 3/36 524/262 |
| 2008/0044735 A1 | * | 2/2008 | Ryu ....................... | C07F 7/1836 429/331 |
| 2010/0069531 A1 | | 3/2010 | Sakamoto et al. | |
| 2010/0330433 A1 | * | 12/2010 | Amine .................. | H01M 6/181 429/302 |
| 2012/0019767 A1 | | 1/2012 | Cadet et al. | |
| 2012/0135313 A1 | * | 5/2012 | West .................... | H01M 10/052 429/300 |
| 2014/0127140 A1 | * | 5/2014 | Ferritto .................... | A61Q 5/12 424/43 |
| 2014/0177053 A1 | * | 6/2014 | Cadet ..................... | G02B 1/115 359/507 |
| 2014/0179815 A1 | * | 6/2014 | Walia ................... | C08G 18/289 521/154 |
| 2014/0302318 A1 | * | 10/2014 | Ferritto ................... | C07F 7/184 428/391 |
| 2015/0266271 A1 | * | 9/2015 | Okamoto ............ | C09K 3/1006 428/413 |
| 2015/0322097 A1 | * | 11/2015 | Ferritto ................. | C07F 7/1876 536/56 |

FOREIGN PATENT DOCUMENTS

| | | |
|---|---|---|
| CN | 1451471 A | 10/2003 |
| JP | 5854080 A | 3/1983 |
| JP | 10059828 A * | 3/1998 |
| TW | 201502131 A | 1/2015 |
| WO | WO-94/28229 A2 | 12/1994 |
| WO | WO-2013/066911 A1 | 5/2013 |
| WO | WO-2013/127775 A1 | 9/2013 |
| WO | WO-2014/182830 A1 | 11/2014 |
| WO | WO-2014/182841 A1 | 11/2014 |

OTHER PUBLICATIONS

Machine Translation of JP-10059828-A (Year: 2018).*

(Continued)

*Primary Examiner* — Liam J Heincer
(74) *Attorney, Agent, or Firm* — Schwegman Lundberg & Woessner, P.A.

(57) ABSTRACT

The present disclosure relates to compositions comprising: an organosilane having the formula: $(R^1)(3\text{-}n)(R^2O)_n SiR^3O(CH_2CH_2O)_a(C_3H_6O)_b R^4$ wherein: n is 1 or 2; a≥1, b may vary from 0 to 30, with the proviso a≥b; $R^1$ is a hydrocarbon group containing 1 to 12 carbon atoms; $R^2$ is hydrogen or an alkyl group containing 1 to 6 carbon atoms; $R^3$ is a divalent hydrocarbon group containing 2 to 12 carbon atoms; and $R^4$ is hydrogen, $R^1$, or an acetyl group; and at least one of a thermoplastic resin, a thermoset resin, and an elastomer. The present organosilane compositions may be useful for treating various surfaces to render them, among other things, more hydrophilic.

9 Claims, No Drawings

(56) References Cited

OTHER PUBLICATIONS

"Database WPI Week 198319", Thomson Scientific, London, AN 1983-45023K, XP002728998.
"International Application Serial No. PCT/US2014/037175, International Search Report dated Jul. 17, 2014", 4 pgs.
"International Application Serial No. PCT/US2014/037175, Written Opinion dated Jul. 17, 2014", 4 pgs.
"International Application Serial No. PCT/US2014/037188, International Search Report dated Sep. 9, 2014", 4 pgs.
"International Application Serial No. PCT/US2014/037188, Written Opinion dated Sep. 9, 2014", 7 pgs.
Brook, M A, et al., "Elastomeric hydrogels by polymerizing silicone microemulsions", Chemical Communications [6015D], Royal Society of Chemistry, Gb, vol. 47, No. 31,, 3 pgs.
"International Application Serial No. PCT/US2014/037175, International Preliminary Report on Patentability dated Nov. 19, 2015", 6 pgs.
"International Application Serial No. PCT/US2014/037188, International Preliminary Report on Patentability dated Nov. 19, 2015", 9 pgs.

* cited by examiner

HYDROPHILIC ORGANOSILANES

CLAIM OF PRIORITY

This application is a U.S. national stage application filed under 35 U.S.C. § 371 from International Application Serial No. PCT/US2014/037175, which was filed May 7, 2014, and published as WO 2014/182830 on Nov. 13, 2014, and which claims the benefit of priority to International Application No. PCT/CN2013/075345, filed May 8, 2013, and the benefit of priority to Polish Application No. P.403810, filed May 8, 2013, the disclosures of which are incorporated by reference as if reproduced herein and made a part hereof in their entirety, and the benefit of priority of each of which is claimed herein.

BACKGROUND

There is an on-going need to develop improved composition treatments to render various surfaces more hydrophilic. Many such surfaces are naturally hydrophobic or have limited ability to absorb water or polar liquids or have these liquids wet the surface. These surfaces may include substrates such as fibers, textiles, plastics, glass, or metals. Treating the surface to render them more hydrophilic may improve properties such as moisture pick up, absorbency, surface wetting, breathability and the like. Many of the hydrophilic surface treatments are based on the physical absorption of the treatment molecules with a surface. As such, the treatments are not robust and are easily washed off or removed.

Thus, there is a need to identify materials that can be used to treat various surfaces to render them hydrophilic. Furthermore, there is a need to identify such hydrophilic materials that permanently (or substantially permanently or semipermanently) modify a surface and more permanently (or substantially permanently or semipermanently) bond to the surface.

SUMMARY

The present inventors have discovered certain organosilanes that improve the hydrophilicity of treated surfaces. In particular, the present disclosure relates to compositions comprising an organosilane having the formula;

$(R^1)_{(3-n)}(R^2O)_n SiR^3O(CH_2CH_2O)_a(C_3H_6O)_b R^4$ where n is 1 or 2,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group.

The present organosilanes, or compositions containing reaction products derived from the present organosilanes, are particularly useful to treat various surfaces to render them, among other things, more hydrophilic. In particular, the present organosilanes and related compositions are useful to treat textiles, fibers, or hard surfaces to improve, among other properties, the hydrophilicity of the surface. The treated surface may have improved absorbency, moisture pick up, or surface wettability properties. Furthermore, subsequent surface treatments with the present compositions are more permanent (or substantially more permanent or semipermanent) than many treatments.

DESCRIPTION

The present disclosure relates to compositions comprising an organosilane, or reaction products therefrom, having the formula;

$(R^1)_{(3-n)}(R^2O)_n SiR^3O(CH_2CH_2O)_a(C_3H_6O)_b R^4$ where the subscript "n" is 1 or 2, alternatively n is 2,
the subscript "a" is equal to or greater than 1,
the subscript "b" varies from 0 to 30,
  with the proviso that a≥b,
$R^1$ is a hydrocarbon group containing 1 to 12 carbon atoms,
  alternatively $R^1$ is an alkyl group or a phenyl group,
    alternatively $R^1$ is methyl,
$R^2$ is hydrogen or an alkyl group contain 1 to 6 carbon atoms,
  alternatively $R^2$ is methyl or ethyl,
    alternatively $R^2$ is ethyl,
$R^3$ is a divalent hydrocarbon group containing 2 to 12 carbon atoms,
  alternatively $R^3$ contains 2 to 6 carbon atoms,
    alternatively $R^3$ is propylene, or isobutylene,
      alternatively $R^3$ is —CH$_2$CH$_2$C(CH$_3$)$_2$—
        alternatively $R^3$ is propylene,
$R^4$ is hydrogen, $R^1$, or an acetyl group,
  alternatively $R^4$ is methyl.

The present organosilanes contain a polyoxyalkylene moiety which is predominately a polyoxyethylene chain as designated by (CH$_2$CH$_2$O)$_a$ in the above formula. The polyoxyalkylene group comprises predominately oxyethylene units (C$_2$H$_4$O), but may also contain oxypropylene units (C$_3$H$_6$O), oxybutylene units (C$_4$H$_8$O), or mixtures thereof. When the polyoxyalkylene group comprises a mixture of (C$_2$H$_4$O), (C$_3$H$_6$O), and/or (C$_4$H$_8$O) units, the oxyalkylene groups are typically randomized with the group but can also be blocked. Typically, the polyoxyalkylene group comprises a majority of polyoxyethylene units, as defined on a molar basis and indicated in the above formula by the "a" subscript. The subscript "a" is equal to or greater than 1,
  alternatively a may vary from 4 to 30,
    alternatively a may vary from 4 to 20,
      alternatively a may vary from 4 to 10,
        alternatively a may vary from 5 to 8,
          alternatively a is 7.
The subscript "b" varies from 0 to 30,
  alternatively b may vary from 1 to 30,
    alternatively b may vary from 1 to 20,
      alternatively b may vary from 10 to 20,
        alternatively b may vary from 15 to 20,
with the proviso that a≥b.

In one embodiment, the organosilane has the following average formula;

(CH$_3$)(CH$_3$CH$_2$O)$_2$SiCH$_2$CH$_2$CH$_2$O(CH$_2$CH$_2$O)$_7$CH$_3$.

In one embodiment, the organosilane has the following average formula;

(CH$_3$)(CH$_3$O)$_2$SiCH$_2$CH$_2$C(CH$_3$)$_2$O(CH$_2$CH$_2$O)$_{18}$(C$_3$H$_6$O)$_{18}$H.

The present organosilanes may be prepared by any method known in the art for preparing organosilanes, or alternatively the organosilanes may be prepared by the process as discussed below.

The organosilane may be prepared by a process comprising reacting:

a) an organosilane of the formula $(R^1)_{(3-n)}(R^2O)_n SiH$,
   where $R^1$ is a hydrocarbon group containing 1 to 12 carbon atoms,
   $R^2$ is hydrogen or an alkyl group contain 1 to 6 carbon atoms,
   the subscript n is 1 or 2, alternatively n is 2,
b) a polyoxyalkylene of the formula $R^5O(CH_2CH_2O)_a(C_3H_6O)_b R^4$
   where the subscript "a" is equal to or greater than 1,
   the subscript "b" varies from 0 to 30,
   with the proviso that a≥b,
   $R^4$ is hydrogen, $R^1$, or an acetyl group,
   $R^5$ is an unsaturated aliphatic hydrocarbon group containing 2 to 12 carbon atoms, and
c) a hydrosilylation catalyst.

Component a) is an organosilane of the formula $(R^1)_{(3-n)}(R^2O)_n SiH$. Alternately, it is possible for two or more H groups to be present on the Si atom, in which case $R^1$ would be zero. In cases such as this, two polyether groups would subsequently be grafted onto the Si atom. Representative examples of organosilanes suitable as component a) in the present process include;

$(CH_3)(CH_3CH_2O)_2SiH$, $(CH_3)(CH_3O)_2SiH$, $(CH_3CH_2)(CH_3CH_2O)_2SiH$, $(CH_3CH_2)(CH_3O)_2SiH$ $(CH_3)(HC(CH_3)_2O)_2SiH$ $(CH_3CH_2O)_2SiH_2$

The polyoxyalkylene useful as component b) can be any polyoxyalkylene that is terminated at one molecular chain end with an unsaturated aliphatic hydrocarbon group containing 2 to 12 carbon atoms. The polyoxyalkylene may result from the polymerization of ethylene oxide, propylene oxide, butylene oxide, 1,2-epoxyhexane, 1, 2-epoxyoctane, cyclic epoxides such as cyclohexene oxide or exo-2,3-epoxynorborane. The polyoxyalkylene group comprises predominately oxyethylene units ($C_2H_4O$), but may also contain minor amounts of oxypropylene units ($C_3H_6O$), oxybutylene units ($C_4H_8O$), or mixtures thereof. Typically, the polyoxyalkylene group comprises a majority of oxyethylene units, as defined on a molar basis and indicated in the above formula by the "a" subscript. When present, the oxypropylene units are indicated in the above formula by the "b" susbscript. The unsaturated aliphatic hydrocarbon group can be an alkenyl or alkynyl group. Representative, non-limiting examples of the alkenyl groups are shown by the following structures; $H_2C=CH-$, $H_2C=CHCH_2-$, $H_2C=CHC(CH_3)_2-H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures; $HC\equiv C-$, $HC\equiv CCH_2-$, $HC\equiv CCH(CH_3)-$, $HC\equiv CC(CH_3)_2-$, and $HC\equiv CC(CH_3)_2CH_2-$.

In one embodiment, $R^5$ in the polyoxyalkylene of the formula is $H_2C=CHCH_2-$, or $H_2C=CHC(CH_3)_2-$. The $H_2C=CHC(CH_3)_2-$ group is a preferred embodiment for preparing the present organosilanes having a greater purity since this hydrocarbon group is not susceptible to rearrangements during the hydrosilylation reaction.

Polyoxyalkylenes having an unsaturated aliphatic hydrocarbon group at one molecular terminal are known in the art, and many are commercially available. Representative, non-limiting examples of polyoxyalkylenes having an unsaturated aliphatic hydrocarbyl at one molecular terminal include;

$H_2C=CHCH_2O[C_2H_4O]_a H$ $H_2C=CHCH_2O[C_2H_4O]_a[C_3H_6O]_b H$ $H_2C=CHCH_2O[C_2H_4O]_a CH_3$ $H_2C=CHC(CH_3)_2O[C_2H_4O]_a CH_3$ $H_2C=CHC(CH_3)_2O[C_2H_4O]_a[C_3H_6O]_b H$ $H_2C=CHCH_2O[C_2H_4O]_a C(O)CH_3$ $H_2C=C(CH_3)CH_2O[C_2H_4O]_a H$ $HC\equiv CCH_2O[C_2H_4O]_a H$ $HC\equiv CC(CH_3)_2O[C_2H_4O]_a H$ where a and b are as defined above.

Polyoxyalkylenes having an unsaturated aliphatic hydrocarbon group at one molecular terminal are commercially available from numerous suppliers including; NOF (Nippon Oil and Fat, Tokyo, Japan), Clariant Corp. (Switzerland), and Dow Chemical Corp. (Midland, Mich.). Commercial examples of these materials include Uniox MUS-4 from NOF, Polyglykol AM 450 from Clariant, and SF 400 and SF 443 from Dow Chemical Corp.

The amounts of components a) and b) used in the hydrosilylation reaction may vary. The molar ratio of the SiH units of component a) to the aliphatic unsaturated groups of component b) may range from 10/1 to 1/10, alternatively from 5/1 to 1/5, or alternatively from 1/1 to 1/2. Typically, the amounts of components a) and b) are selected to provide molar excess of the unsaturated groups of component b) to the SiH groups in component a).

Component c) is a hydrosilylation catalyst. The hydrosilylation catalyst may be any suitable Group VIII metal based catalyst selected from a platinum, rhodium, iridium, palladium or ruthenium. Group VIII group metal containing catalysts useful to catalyze curing of the present compositions can be any of those known to catalyze reactions of silicon bonded hydrogen atoms with silicon bonded unsaturated hydrocarbon groups. The preferred Group VIII metal for use as a catalyst to effect cure of the present compositions by hydrosilylation is a platinum based catalyst. Some preferred platinum based hydrosilylation catalysts for curing the present composition are platinum metal, platinum compounds and platinum complexes.

Suitable platinum catalysts are described in U.S. Pat. No. 2,823,218 (commonly referred to as "Speier's catalyst) and U.S. Pat. No. 3,923,705. The platinum catalyst may be "Karstedt's catalyst", which is described in Karstedt's U.S. Pat. Nos. 3,715,334 and 3,814,730. Karstedt's catalyst is a platinum divinyl tetramethyl disiloxane complex typically containing about one-weight percent of platinum in a solvent such as toluene. Alternatively the platinum catalyst may be a reaction product of chloroplatinic acid and an organosilicon compound containing terminal aliphatic unsaturation, as described in U.S. Pat. No. 3,419,593. Alternatively, the hydrosilylation catalyst is a neutralized complex of platinum chloride and divinyl tetramethyl disiloxane, as described in U.S. Pat. No. 5,175,325.

Further suitable hydrosilylation catalysts are described in, for example, U.S. Pat. Nos. 3,159,601; 3,220,972; 3,296,291; 3,516,946; 3,989,668; 4,784,879; 5,036,117; and 5,175,325 and EP 0 347 895 B1.

The hydrosilylation catalyst may be added in an amount equivalent to as little as 0.001 part by weight of elemental platinum group metal, per one million parts (ppm) of the total reaction composition. Typically, the concentration of the hydrosilylation catalyst in the reaction composition is that capable of providing the equivalent of at least 1 part per million of elemental platinum group metal. A catalyst concentration providing the equivalent of 1 to 500, alternatively 50 to 500, alternatively 50 to 200 parts per million of elemental platinum group metal may be used.

The reaction effected in the present process is a hydrosilylation reaction, wherein the SiH units of component a) react with the unsaturated aliphatic hydrocarbon group of component b) form an Si—C bond. The reaction may be conducted under those conditions known in the art for effecting hydrosilylations reactions.

The hydrosilylation reaction can be conducted neat or in the presence of a solvent. The solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent can be up to 70 weight percent, but is typically from 20 to 50 weight percent, said weight percent being based on the total weight of components in the hydrosilylation reaction. The solvent used during the hydrosilylation reaction can be subsequently removed from the resulting organosilane by various known methods.

Additional components can be added to the hydrosilylation reaction which are known to enhance such reactions. These components include salts such as sodium acetate which have a buffering effect in combination with platinum catalysts.

The present disclosure also relates to the organosilane compositions produced by the aforementioned process.

The present organosilanes contain at least one alkoxy group, as represented by ($R^2O$) in the formula above. As such, the present organosilanes will hydrolyze in aqueous medium, and may further condense to form oligomeric or higher molecular weight polymeric siloxanes. Thus, the present disclosure relates to the reaction products resulting from the hydrolysis and/or condensation of the aforementioned organosilanes. The present organosilanes, or subsequently produced oligomeric or polymeric siloxanes derived from the organosilanes, may react with hydroxyl functional compounds or surfaces. Since the present organosilanes contain a polyalkylene oxide chain that is predominately ethylene oxide, the present organosilanes may be considered as "hydrophilic". Thus, the present organosilanes may be used to treat various surfaces to impart greater "hydrophilicity" to the surface. Furthermore, the reactivity of the silane moiety may allow the present compositions to bond to various surfaces to provide a longer lasting, more durable hydrophilic treatment. For example, when compositions comprising the present organosilanes are applied to various surfaces (e.g., the surfaces of a fibers), the organosilanes can react with functional groups on the surfaces (e.g., epoxy, hydroxyl, carbinol, and ester) thereby forming a substantially permanent bond with the surface. The same reactions can occur when compositions comprising the present organosilanes are incorporated into (e.g., blended with) thermoplastic resins, thermoset resins, and the like, either as the resins are made or into molten resin.

When used to treat various surfaces or when incorporated into bulk materials (e.g., thermoplastic and thermoset resins) the organosilanes, or reaction products derived therefrom, may be applied or incorporated neat, as an aqueous solution, as a solution in an organic solvent, or as a component in a multi-component formulation. When applied or incorporated as a solution, additional components such as acids or bases to buffer the pH may be added to the solution that are known to enhance the hydrolysis and condensation of alkoxysilanes.

The present organosilanes, or reaction products derived therefrom, may be used to decrease the surface energy and the water contact angles of various surfaces, which is indicative of increased hydrophilicity of those surfaces. In some embodiments, the organosilanes, or reaction products derived therefrom, may be used to impart anti-fogging properties, water sheeting properties, higher gloss, higher surface smoothness, etc., to surfaces, including films (e.g., agricultural film and automotive window film), while maintaining high transparency. The treatments may be longer lasting or more durable than conventional treatments. In some embodiments, the organosilanes, or reaction products derived therefrom, may improve one or more of the following properties: wet out properties, dispersion properties, solubility properties, adhesion properties, mechanical properties, optical properties, surface properties, flame retardant properties, surface smoothness, may lower the coefficient of friction of a surface, etc.

Surfaces suitable for treatment include various hard surfaces such as glass, metals, plastics, minerals, and woods. The surfaces further include fibers, fabrics or textile surfaces. Fibers or textiles that can be treated with the treatment composition include natural fibers such as cotton, silk, linen, wool, flax, kapok, hemp, flax, ramie, alpaca, cashmere, mohair, sisal, abaca, jute, kenaf, camel hair, etc.; regenerated fibers such as lycocell, rayon, acetate, viscose, cupra, polynosic, high wet modulus rayon, solvent-spun cellulose, etc.; synthetic fibers such as polyesters, polyamides, polyacrylonitriles, polyolefins (e.g., polyethylenes and polypropylenes), vinylon, polyvinyl chloride, promix, fiberglass, aramids, azlons, modacrylics, novoloids, nytrils, spandex, vinal, vinyon etc.; and combinations, and blends thereof. The form of the fibers can include threads, filaments, tows, yarns, woven fabrics, knitted materials, non-woven materials, paper, carpet, and leather. In a further embodiment, the fiber is a cellulosic fiber such as cotton.

The term "polyamide" or "polyamides" refers broadly to any long-chain polymer having recurring amide groups as an integral part of the polymer chain. Examples of polyamides include nylon 6; nylon 6,6; nylon 1,1; and nylon 6,10.

The term "polyester" refers broadly to any long-chain polymer having recurring ester groups. Examples of polyesters include aromatic polyesters, such as polyethylene terephthalate (PET), polypropylene terephthalate, polybutylene terephthalate (PBT), polytrimethylene terephthalate (PTT), and polytriphenylene terephthalate, and aliphatic polyesters, such as polylactic acid (PLA) and polyglycolide and the like.

The term "polyolefin" includes, for example, polypropylene, polyethylene, and combinations thereof.

"Polyaramid" includes, for example, poly-p-phenyleneteraphthalamid (i.e., Kevlar™), poly-m-phenyleneteraphthalamid (i.e., Nomex™), and combinations thereof.

Other suitable fibers include, but are not limited to, the fibers disclosed in Published U.S. Patent Appl. Nos. 2012/0277356; 2011/0015310; 2008/0153735; and 2002/0160675, the entireties of all of which are incorporated by reference as if fully set forth herein.

The fiber treatment composition comprising the present organosilanes, oligomeric or polymers derived therefrom, can be applied to the fiber and/or textile during making the fibers or textiles, or later via a post application process. After application, carriers (if any) can be removed from the treatment composition for example by drying the composition at ambient or elevated temperature. The amount of treatment composition applied to the fibers and textiles is typically sufficient to provide 0.1 to 15 weight percent of the composition on the fibers and textiles, based on their dry weight, preferably in an amount of 0.2 to 5 weight percent based on the dry weight of the fiber or textile.

In some embodiments, the organosilanes, or reaction products derived therefrom, may be incorporated into a variety of compositions including, but not limited to, paints and other coatings, including marine coatings and architectural coatings; inks (e.g., ink-jet printer inks); and thermoplastic and/or thermoset compositions (e.g., thermoplastic resins; thermoset resins; and rubber compounds, including thermoplastic elastomers), including thermoplastic and/or thermoset formulations that can be formed into fibers, textiles or other articles of manufacture, including films, tires, automotive parts, etc.

Examples of suitable thermoset resins include, but are not limited to, those commonly known in the art, such as natural rubbers, crosslinked synthetic rubbers such as polyisoprene, polybutadiene, neoprene, acryl, silicone and ester rubbers, thermosetting fluoroelastomers such as those made by crosslinking polymerized vinyl compounds such as hexafluoropropylene, vinylidene fluoride, tetrafluoroethylene, chlorotrifluoroethylene, and copolymers thereof (e.g., those manufactured under the tradename of Viton™), or by crosslinking polymerized alkyl acrylates and/or alkyl methacrylates (hereinafter referred to as "alkyl acrylate" monomers or simply "alkyl acrylates"), such as hexafluorobutyl methacrylate, and hexafluorobutyl acrylate. Other examples of suitable thermoset resins include polyurethanes, epoxy resins, phenoxy resins, cyanate esters, polyimides, phenolic resins, polyphenol-formaldehyde, polymelamine-formaldehyde, polyurea-formaldehyde, bis-maleimide triazine, and cross-linked versions of poly(n-alkyl acrylates), polyesters, polyolefins, polystyrenes, polyvinyl chlorides, vinyl esters and polyamides.

Examples of suitable thermoplastic resins include, but are not limited to, styrene-based polymers such as polystyrene (including atactic, syndiotactic and isotactic polystyrene), halogen-substituted styrene polymers, styrene acrylonitrile copolymers, acrylonitrile-butadiene-styrene (ABS) resins, styrene-butadiene copolymers, styrene-butadiene-styrene (SBS) block copolymers, blends of styrene-acrylonitrile copolymer and ethylene-styrene interpolymer, polycarbonate/acrylonitrile-butadiene-styrene terpolymer alloys, and SEBS resins, polyacrylonitrile, condensation polymers such as polyesters including polyethylene terephthalate, polybutylene terephthalate (PBT), polyarylate, and the like, polycarbonates (including impact-modified polycarbonate), polyethers such as polyphenyleneoxide, maleic anhydride grafted polyphenyleneoxide, maleic anhydride grafted olefinic elastomers and plastomers, polysulfone, polyethersulfone, polyarylsulfone, polyphenylene ether, and the like, condensed polymers such as polyamide (6, 6/6, 6/10, 6/12, 11 or 12, and the like) and polyoxymethylene, polyphenylenesulfide (PPS), acryl-based polymers such as polyacrylic acid, poly(n-butyl methacrylate), poly(n-butyl acrylate), and polymethyl methacrylate, halogen-substituted acrylates such as hexafluorobutyl methacrylate and hexafluorobutyl acrylate polyacrylamides, polyolefins such as polyethylene (low density polyethylene (LDPE), medium and high density polyethylene, linear low density polyethylene (LLDPE), high density polyethylene (HDPE), and the like), polypropylene (including isotactic polypropylene and blends of isotactic polypropylene and syndiotactic polypropylene) blends of isotactic polypropylene and polyethylene, polybutene, poly(4-methylpentene-1), ethylene-propylene copolymers, poly(ethylene/1-butylene), poly(propylene/1-butylene), poly(ethylene/propylene/1-butylene), poly(ethylene butyrate), and poly(polyethylene naphthalate), halogen substituted vinyl polymers such as polyhexafluoropropylene, polytetrafluoroethylene, polyvinylidene fluoride, polyvinyl chloride, polyvinylidene chloride, polyvinyl fluoride, polyvinylidene dichloride, vinylidene chloride-vinyl chloride copolymers, vinylidene chloride-methylacrylate copolymers, and the like, polyvinylmethylether, other vinyl containing compounds such as ethylene-vinyl alcohol polymers and polyvinyl alcohols, ethylene vinyl acetate, and other vinyl containing compounds having an epoxy group, such as glycidyl methacrylate, glycidyl acrylate, vinyl glycidyl ether, glycidyl ether of hydroxyalkyl(meth)acrylate, glycidyl ether of polyalkyleneglycol(meth)acrylate, and glycidylitaconate, among which glycidyl methacrylate is particularly preferred. Also included for example are copolymers of styrene and substituted styrene (e.g., styrene/p-methylstyrene copolymers. These copolymers can be atactic, isotactic, or syndiotactic.

Further examples of thermoplastic resins include polyacetals, polyamide-imides, polypthalamides, polyetherimides, polyformaldehydes such as Delrin™, polyethyleneimine, poly-N-vinylcarbazole, polytetrafluoroethylene, fluorinated ethylene propylene, perfluoroalkoxy, polychlorotrifluoroethylene, ethylene tetrafluoroethylene, polyetherketone, polyether etherketone, polyether ketone ether ketone, polyoxymethylene(acetal) homopolymer copolymers, polyester urethane, polyether urethane, ethylene/vinyl acetate copolymer, copolymers of ethylene or propylene with other alpha-olefins, copolymers of acrylonitrile-butadiene-styrene (ABS), copolymers of acrylonitrile and styrene impact-modified with ethylene-propylene rubber or ethylene/propylene/alpha-olefin rubber or butyl acrylate rubber, blends of ABS and polycarbonate, blends of ABS and polyvinyl chloride (PVC), PVC, copolymers of styrene and butadiene, copolymer of styrene and butadiene that also contains ethylene-propylene rubber or ethylene/propylene/alpha-olefin rubber or butyl acrylate rubber, thermoplastic elastomer, or thermoplastic vulcanizate, polylactide, polyphenylene oxide, amorphous glassy polymers, preferably of cellulose acetate, cycloolefin copolymers such as Topaz™ manufactured by Ticona, polymethyl methacrylate, glycol-modified polyester, blends of glycol-modified polyester, optionally amorphous co-polyester, maleic anhydride grafted ethylene-methyl acrylate copolymer, ethylene-methyl acrylate-glycidyl methacrylate copolymer, maleic anhydride functionalized styrene-ethylene-butene block copolymer, styrene-isoprene-styrene block copolymer, amorphous thermoplastic polyester resins having a glass transition temperature ($T_g$) of above 50.degree. C., amorphous polyamide or copolymer polyamide having a $T_g$ of above 120° C., glycol-modified polyester, amorphous polyurethanes or their blends with at least 60 wt. % of glycol-modified polyester, and impact-modified poly(methyl methacrylate).

Yet a further example of a thermoplastic resin includes one or more copolymers selected from a-b type block copolymers, a-b-a type block copolymers, b-a-b type block copolymers, a grafted b copolymers and b grafted a copolymers, where a is a non-reactive block with a glass transition temperature or melting transition temperature higher than that of a rubbery b block. In the art, many such block copolymers and blends thereof are known as thermoplastic elastomers. As portion a of the a-b, a-b-a or b-a-b type block copolymer, examples include atactic polystyrene, polymethylmethacrylate. As portion b, one or more polymers or copolymers selected from conjugated diene, hydrogenated product of conjugated diene, conjugated diene modified with acid anhydride, hydrogenated product of conjugated diene modified with acid anhydride, organopolysiloxane and polyalkylacrylate can be given along with their halogenated and partially halogenated homologs. Examples of portion b include polymers and copolymers of isoprene, butadiene, hydrogenated butadiene, hydrogenated isoprene, dimethylsiloxane, butadiene modified with maleic anhydride, hydrogenated product of butadiene modified with maleic anhydride, isoprene modified with maleic anhydride, hydrogenated product of isoprene modified with maleic anhydride, phenylmethylsiloxane, methyl-3,3,3-trifluoropropylsiloxane, n-butyl acrylate, 2-ethylhexyl acrylate, 2-ethylhexyl methacrylate, and 1H,1H,3H-tetrafluoropropylacrylate.

Graft copolymers which can be used are indicated in terms of a grafted b copolymers or b grafted a copolymers. Examples are a styrene-butadiene block copolymer rubber (SB, SBS, BSB), rubbers obtained by partially or completely hydrogenating the butadiene portion of a styrene-butadiene block copolymer (SEBS, SEB), a styrene-isoprene block copolymer rubber (SI, SIS, ISI), rubbers obtained by partially or completely hydrogenating the isoprene portion of a styrene-isoprene block copolymer (SEP, SEPS), SBS modified with maleic anhydride, SEBS modified with maleic anhydride, SEP modified with maleic anhydride and SIS modified with maleic anhydride.

Other elastomers include; an AABS elastomer, obtained by adding acrylonitrile and styrene to a rubber latex which has been obtained by copolymerizing butadiene and alkyl acrylate, and then graft polymerizing them, and a SBR elastomer (trade name: Metablen IP-2, produced by Mitsubishi Rayon Co., Ltd.), obtained by graft polymerizing styrene to polybutadiene. These rubber-like polymers are core shell type rubbers.

The thermoset or thermoplastic resin or resins may be modified with supplemental additives including, but not limited to, antioxidants, coloring agents such as pigments and dyes, flame retardants, process aids, antistatic agents, impact modifiers, nucleating agents, flow aids, ignition resistant additives, coupling agents, lubricants, antiblocking agents, mold release additives, plasticizers, ultraviolet ray inhibitors, thermal stabilizers. In some embodiments, the organosilanes, or reaction products derived therefrom, may improve, among other things, the dispersion of one or more of the aforementioned supplemental additives.

The thermoset or thermoplastic resin or resins may also include fillers or reinforcing agents. Such fillers and reinforcing agents can be fibrous, granular or powder in form and include, but are not limited to, fibrous components such as glass fiber, carbon fiber, alumina fiber, and granular or powder components such as silica, clay, talc, carbon black, graphite, titanium dioxide, mica, calcium carbonate, calcium sulfate, barium carbonate, magnesium carbonate, magnesium sulfate, barium sulfate, oxysulfate, tin oxide, alumina, kaolin, silicon carbide, and metal powder. In some embodiments, the organosilanes, or reaction products derived therefrom, may improve, among other things, the dispersion of one or more of the aforementioned fillers and/or reinforcing agents.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Example 1

Preparation of Poly (EO) Methyl 3-(Methyldiethoxysilyl) Propyl Ether

PG SF-Allyl EO7-Me (463.73 g; UNIOX MUS-4 from NOF Corporation) and sodium acetate (0.05 g; from Fisher Biotech) were loaded in a 2 L 3-necked round-bottomed flask (RBF) fitted with a crescent-shaped paddle stirring rod, a Claisen adaptor itself fitted with a water cooled condenser and a 250 mL additional funnel loaded with methyldiethoxylsilane (136.52 g; from Gelest, Inc), and a thermometer adaptor itself fitted with a thermal couple, all under nitrogen purge. The reaction mixture was heated to 60° C. when 20 wt. % or 28 g of methyldiethoxylsilane was fed in the RBF immediately followed by the addition of 1% Dow Corning® 2-0707 INT catalyst in IPA (~400 μL or 6 ppm). The exotherm observed instantaneously was 18° C. The remaining methyldiethoxylsilane in the additional funnel was being dispensed into the RBF at ~1.21 g/min rate while temperature was set at 80° C. and being maintained below 85° C. throughout the addition. The second charge of 1% Dow Corning® 2-0707 INT catalyst in IPA (~500 μL or 7 ppm) was done after the first hour of silane addition and ~5° C. exotherm was seen. When all methyldiethoxylsilane was in the RBF, the temperature was set at 85° C. set point and the third addition of 1% Dow Corning® 2-0707 INT catalyst in IPA (~500 μL or 7 ppm) was added while no exotherm was observed. The product mixture was then allowed to reflux for another hour for hydrosilylation completion. Once the reaction was determined to be done, residual SiH was measured by IR which was 34 ppm at peak 2150 cm$^{-1}$. On the following day, the Claisen adapter was replaced by a water cooled condenser fitted with a 250 mL round-bottomed flask. The set-up was connected to vacuum for stripping. The product mixture was stripped for 1 h under 10-40 mmHg vacuum pressure at 90° C. The final residual SiH content measured by IR was 4 ppm at 2150 cm$^{-1}$. The final finished product was pressure-filtered on 20 μm sized filter paper to remove sodium acetate.

Example 2

Preparation of Poly (EO) Methyl 3-(Methyldimethoxysilyl) Propyl Ether

PG SF-Allyl EO7-Me (489.378 g; UNIOX MUS-4 from NOF Corporation) and sodium acetate (0.1 g; from Fisher Biotech) were loaded in a 2 L 3-necked round-bottomed flask (RBF) fitted with a crescent-shaped paddle stirring rod, a Claisen adaptor itself fitted with a water cooled condenser and a 250 mL additional funnel loaded with Dow Corning® Z-6701 Silane (110.622 g), and a thermometer adaptor itself fitted with a thermal couple, all under nitrogen purge. The reaction mixture was heated to 45° C. when 10 wt. % or 11 g of Z-6701 silane was fed in the RBF immediately followed by the addition of 1% Dow Corning® 2-0707 INT catalyst in IPA (~400 μL or 6 ppm). The exotherm observed instantaneously was 2-3° C. The remaining Z-6701 in the additional funnel was being dispensed into the RBF at ~1.67 g/min rate while temperature set at 53° C. plus 2° C. exotherm was maintained throughout the addition. When all Z-6701 was in the RBF, the temperature of mixture dropped back to the 53° C. set point and hence, there was a second addition of 1% Dow Corning® 2-0707 INT catalyst in IPA (~500 or 7 ppm). The mixture was then held for another 2 h to allow reaction gone for completion in which the third addition of 1% Dow Corning® 2-0707 INT catalyst in IPA (~500 μL or 7 ppm) were made after the first hour of reflux. A constant 2° C. exotherm was observed after each time the catalyst was added and had lasted for 1 h except for the last addition which lasted only 30 minutes. Once the reaction was determined to be done, residual SiH was measured by IR which was 35 ppm at peak 2150 $cm^{-1}$. On the following day, the Claisen adapter was replaced by a water cooled condenser fitted with a 250 mL round-bottomed flask. The set-up was connected to vacuum for stripping. The product mixture was stripped for 1 h under 10-20 mmHg vacuum pressure at 60° C. The final residual SiH content measured by IR was 4 ppm at 2150 $cm^{-1}$. The final finished product was pressure-filtered on 20 μm sized filter paper to remove sodium acetate.

Example 3

Preparation of Poly (EO) Hydroxyl 3-(Methyldiethoxysilyl) Propyl Ether

PG SF-Allyl EO7-OH (191.85 g; from Dow Chemical Company) and sodium acetate (0.05 g; from Fisher Biotech) were loaded in a 500 mL 3-necked round-bottomed flask (RBF) fitted with a crescent-shaped paddle stirring rod, a Claisen adaptor itself fitted with a water cooled condenser and a 250 mL additional funnel loaded with methyldiethoxylsilane (58.67 g from Gelest, Inc), and a thermometer adaptor itself fitted with a thermal couple, all under nitrogen purge. The reaction mixture was heated to 60° C. when 10 wt. % or 6 g of methyldiethoxylsilane was dispensed in the RBF immediately followed by the addition of 1% Dow Corning® 2-0707 INT catalyst in IPA (~230 μL or 8 ppm). The exotherm observed instantaneously was 7° C. The remaining methyldiethoxylsilane in the additional funnel was being dispensed into the RBF at ~0.88 g/min rate while temperature was set at 67° C. and being maintained at ~75° C. throughout the addition. When all methyldiethoxylsilane was added to the RBF, the temperature was set at 75° C. to reflux for an hour to allow the reaction to go to completion. The reaction mixture was cooled down to 60° C. and 159 ppm of residual SiH was obtained by IR at peak 2150 $cm^{-1}$. A second addition of 1% Dow Corning® 2-0707 INT catalyst in IPA (~50 μL or ~1.7 ppm) was charged to the reaction mixture, however, no exotherm was detected. The reaction temperature was increased to 80° C. and refluxed for an hour. The residual SiH was measured 126 ppm. On the following day, the product mixture was transferred to a 1 L round-bottomed flask for rotary evaporation. Some material was stripped out while the vacuum pressure was at ~3-4 mmHg and the water bath was at 80° C. This process lasted for two hour and the final product has 13 ppm of SiH left. The final product was pressure-filtered on 20 μm filter paper to remove sodium acetate.

Example 4

Preparation of Poly (EO) Hydroxyl 3-(Methyldimethoxysilyl) Propyl Ether

PG SF-Allyl EO7-OH (80.58 g; from Dow Chemical Company) and sodium acetate (0.03 g; from Fisher Biotech) were loaded in a 250 mL 3-necked round-bottomed flask (RBF) fitted with a crescent-shaped paddle stirring rod, a Claisen adaptor itself fitted with a water cooled condenser and a 250 mL additional funnel loaded with Dow Corning® Z-6701 Silane (20.06 g), and a thermometer adaptor itself fitted with a thermal couple, all under nitrogen purge. The reaction mixture was heated to 45.6° C. when 10 wt. % or 2 g of Dow Corning® Z-6701 Silane was dispensed in the RBF immediately followed by the addition of 1% Dow Corning® 2-0707 INT catalyst in IPA (~60 μL or 5 ppm). The exotherm observed instantaneously was 0.9° C. The remaining Dow Corning® Z-6701 Silane in the additional funnel was being dispensed into the RBF at ~0.21 g/min rate while temperature was set at 50° C. and being maintained at ~49-51° C. throughout the addition. When all methyldiethoxylsilane was added to the RBF, the temperature was set at 57° C. to reflux for 2.5 hours to allow reaction gone for completion. The reaction mixture was cooled down to room temperature and 121 ppm of residual SiH was obtained by IR at peak 2150 $cm^{-1}$. On the following day, extra PG SF-Allyl EO7-OH (5.48 g from Dow Chemical Company) was added to the reaction mixture while holding the reaction at 57±1° C. for 4.5 h, resulting in 20 ppm residual SiH. The Claisen adapter was replaced by a water cooled condenser fitted with a 250 mL round-bottomed flask the day after. The set-up was connected to vacuum for stripping. The product mixture was stripped for 3 h under 10-50 mmHg vacuum pressure at 80° C. The final residual SiH content measured by IR was still 20 ppm at 2150 $cm^{-1}$. The final finished product was pressure-filtered on 20 μm Example 5

Preparation of Poly (EO) Acetate 3-(Methyldimethoxysilyl) Propyl Ether

PG SF-Allyl EO7-Ac (247.77 g) and sodium acetate (0.05 g from Fisher Biotech) were loaded in a 500 mL 3-necked round-bottomed flask (RBF) fitted with a crescent-shaped paddle stirring rod, a Claisen adaptor itself fitted with a water cooled condenser and a 250 mL additional funnel loaded with Dow Corning® Z-6701 Silane (52.98 g), and a thermometer adaptor itself fitted with a thermal couple, all under nitrogen purge. The reaction mixture was heated to 47° C. when 10 wt. % or 5 g of Dow Corning® Z-6701 Silane was dispensed in the RBF immediately followed by the addition of 1% Dow Corning® 2-0707 INT catalyst in IPA (~270 μL or 8 ppm). The exotherm observed instantaneously was 1-2° C. The remaining Dow Corning® Z-6701 Silane in the additional funnel was being dispensed into the RBF at ~0.79 g/min rate while temperature was set at 54° C. and being maintained below 58° C. throughout the addition. When all Dow Corning Z-6701 Silane was added to the RBF, the temperature was set at 54° C. to reflux for an hour to allow reaction gone for completion. 540 ppm of residual SiH was obtained by IR at peak 2150 cm$^{-1}$. Another hour of reflux was proceeded and the residual SiH was measured 300 ppm. On the following day, the Claisen adapter was replaced by a water cooled condenser fitted with a 250 mL round-bottomed flask. The set-up was connected to vacuum for stripping. The product mixture was stripped for a total of 3 h under 20-80 mmHg vacuum pressure at 62° C. The final residual SiH content measured by IR was 28 ppm at 2150 cm$^{-1}$. The final finished product was pressure-filtered on 20 μm sized filter paper to remove sodium acetate.

Example 6

To a three neck round bottom flask was added 0.20 g (2.4 mmoles) of sodium acetate and 171.8 g (0.29 moles) of a polyether containing an allyl end, approximately 12 ethylene oxide units and capped with acetate. Next, 28.2 g (0.21 moles) of methyl diethoxy silane (MDES) was added to the flask. With stirring under N$_2$, the mixture was heated to 75°±5° C. and then 3 ppm of Pt catalyst was added. After a small exotherm (<10°±1° C.) the mixture was maintained at 85°±5° C. for 6 hours. At this point the reaction was 98.9% complete as measured by SiH consumption via FTIR. The mixture was stripped of volatiles by heating to 120°±5° C./5-10 mmHg for 4 hours. Finally, the mixture was cooled to room temperature and filtered through Celite that was supported on a Nylon filter to yield 167 g (83% yield) of a light yellow oil. Characterization of this material indicated that the desired product had been obtained as evidenced by the single peak in the $^{29}$Si NMR at approximately −5.6 ppm.

Example 7

To a three neck round bottom flask was added 0.25 g (3.0 mmoles) of sodium acetate and 189.3 g (97 mmoles) of a polyether containing an allyl end, approximately 18 ethylene oxide units and 18 propylene oxide units and capped with acetate. Next, 10.9 g (81 moles) of methyl diethoxy silane (MDES) was added to the flask. With stirring under N$_2$, the mixture was heated to 75°±5° C. and then 4 ppm of Pt catalyst was added. After a small exotherm (<10°±1° C.) the mixture was maintained at 85°±5° C. for 3 hours. At this point the reaction was 99.6% complete as measured by SiH consumption via FTIR. The mixture was stripped of volatiles by heating to 120°±5° C./5-10 mmHg for 5 hours. Finally, the mixture was cooled to room temperature and filtered through Celite that was supported on a Nylon filter to yield 153 g (76% yield) of a light yellow oil. Characterization of this material indicated that the desired product had been obtained as evidenced by the single peak in the $^{29}$Si NMR at approximately −5.6 ppm.

Example 8

To a three neck round bottom flask was added 0.25 g (3.0 mmoles) of sodium acetate and 168.7 g (0.31 moles) of a polyether containing an allyl end, approximately 12 ethylene oxide units and was not capped. Next, 31.4 g (0.24 moles) of methyl diethoxy silane (MDES) was added to the flask. With stirring under N$_2$, the mixture was heated to 75°±5° C. and then 3 ppm of Pt catalyst was added. After a small exotherm (<10°±1° C.) the mixture was maintained at 85°±5° C. for 3 hours. At this point the reaction was 99.5% complete as measured by SiH consumption via FTIR. The mixture was stripped of volatiles by heating to 120°±5° C.15-10 mmHg for 4 hours. Finally, the mixture was cooled to room temperature and filtered through Celite that was supported on a Nylon filter to yield 149 g (74% yield) of a light yellow oil. Characterization of this material indicated that the desired product had been obtained as evidenced by the single peak in the $^{29}$Si NMR at approximately −5.6 ppm.

Example 9

The following tests were conducted to evaluate the performance of the present organosilanes for their ability to improve the water absorption of cellulosic fibers. Fiber Treatment Test: 6 of the 10 cm×10 cm non-woven 100% cotton fiber weighted 120 gram per square meter (gsm) manufactured by PurCotton™ were used in testing the organosilane of Example 2 (poly (EO) Methyl 3-(Methyl-dimethoxysilyl) Propyl Ether. A circle with area ~13 cm$^2$ was drawn on each fiber sheet, 2 of which were applied the Example 2 organosilane neat in that whole circle area, 2 other sheets were applied with ~29.7% the organosilane of Example 2 in DI water while the last 2 sheets served as control experiment and were untreated. The coated area was then dried at room temperature by blowing air to it for 5 min each. A syringe pump (Model: Cole Parmer 74900 series) was utilized since it could be programmed to dispense liquid at a constant rate and the syringe was filled with DI water. The time for the circle area to fill with liquid by spreading was recorded. It should be recognized that some of the add-on weight to the cloth could include silane+residual moisture that was not removed during the drying process. The results from these tests are summarized below in Table 1.

Example 10

To a 500 ml three neck round bottom flask was added 188.9 g (98.2 mmoles) of a polyether that contains 18 ethylene oxide units, 18 propylene oxide units and is capped with a 3,3-dimethyl-1-propenyl group on one end. The polyether is heated to 40°±3° C. and approximately 5% of total volume of methyldimethoxysilane is added (total volume is 15.7 g, 148 mmoles) to the reaction vessel via an addition funnel. Next, platinum catalyst is added so that the final concentration is 5 ppm in the final mixture, and an exotherm is observed. After the exotherm is complete the remaining methyldimethoxysilane is added from the addition funnel at a rate so that the temperature of the mixture remains below 50° C. Upon the addition of all the methyldimethoxysilane, the reaction vessel is maintained at 50°±3° C. for 3 hours. Next, the volatiles are removed from the product by increasing the flow of N$_2$ through the reaction vessel. A low viscosity liquid is obtained. Analysis by $^1$H, $^{13}$O, $^{29}$Si NMR and FTIR confirms that the desired material has prepared and the level of unreacted polyether is less than 1% on a molar basis and no residual SiH is present.

TABLE 1

| Cloth No. | Cloth Weight (g) | Cloth weight total after treatment and dried (g) | Material Applied on Cloth (g) | Time of wetting-absorption (min'sec") | Remark |
|---|---|---|---|---|---|
| 1 | 1.16 | 1.55 | 0.39 | 46"45 | Example 2 applied neat |
| 2 | 1.2 | 1.55 | 0.35 | 45"73 | Example 2 applied neat |
| 3 | 1.15 | 1.61 | 0.46 | 57"96 | Example 2 applied as a 29.7 wt % aqueous solution |
| 4 | 1.21 | 1.61 | 0.40 | 59"52 | Example 2 applied as a 29.7 wt % aqueous solution |
| 5 | 1.16 | n/a | 0.00 | 1'16"64 | No treatment |
| 6 | 1.21 | n/a | 0.00 | 1'11"66 | No treatment |

TM

Similar tests were performed using the organosilane from Example 1 with the same procedure. There were a total of two experiments done for each batch of material in order to ensure the results given were robust. The summary of the entire application screening test is shown in Table 2 below.

TABLE 2

| Batch Number | Test 1 (sec) | | Test 2 (sec) | | Average Time (sec) | % Average Time Difference |
|---|---|---|---|---|---|---|
| Example 1 applied neat | 46.45 | 45.73 | 41.81 | 42.50 | 44.12 | 41 |
| Example 1 applied neat | 40.26 | 40.80 | 44.83 | 46.57 | 43.12 | 42 |
| Example 1 applied as a 29.7 wt % aqueous solution | 57.96 | 59.52 | 47.60 | 46.40 | 52.87 | 29 |
| Example 1 applied as a 29.7 wt % aqueous solution | 47.81 | 46.57 | 49.52 | 50.48 | 48.60 | 35 |
| Untreated fiber | 76.46 | 71.66 | 75.42 | 74.23 | 74.44 | 0 |

Embodiments of the invention described and claimed herein are not to be limited in scope by the specific embodiments herein disclosed, since these embodiments are intended as illustration of several aspects of the disclosure. Any equivalent embodiments are intended to be within the scope of this disclosure. Indeed, various modifications of the embodiments in addition to those shown and described herein will become apparent to those skilled in the art from the foregoing description. Such modifications are also intended to fall within the scope of the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

As used herein and in the appended claims, the singular forms "a," "an," and "the" include plural reference unless the context clearly dictates otherwise. Thus, for example, a reference to "a reactor" includes a plurality of reactors, such as in a series of reactors. In this document, the term "or" is used to refer to a nonexclusive or, such that "A or B" includes "A but not B," "B but not A," and "A and B," unless otherwise indicated.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

All publications, including non-patent literature (e.g., scientific journal articles), patent application publications, and patents mentioned in this specification are incorporated by reference as if each were specifically and individually indicated to be incorporated by reference.

The invention claimed is:
1. A composition comprising:
an organosilane having the formula:

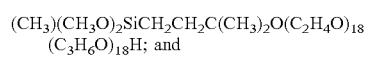

at least one of a thermoplastic resin, a thermoset resin, and an elastomer.

2. The composition of claim 1 further comprising at least one of a mineral filler and a pigment.

3. A surface comprising the composition of claim 1.

4. The surface of claim 3, wherein the surface has at least one of anti-fogging properties and water sheeting properties.

5. The surface of claim 3, wherein the surface is more hydrophilic than a surface lacking the organosilane.

6. The surface of claim 3, wherein the surface comprises a film.

7. The surface of claim 6, wherein the film is an agricultural film or automotive window film.

8. A method for improving the dispersion of additives and/or fillers present in a thermoset or thermoplastic resin comprising adding an effective amount of a composition comprising an organosilane of claim 1 to the thermoset or thermoplastic resin.

9. A method for incorporating an organosilane of claim 1 into a thermoset or thermoplastic resin comprising functional groups, comprising contacting the thermoset or thermoplastic resin with the organosilane; wherein the organosilane reacts with the functional groups, thereby forming a substantially permanent bond with the functional groups.

* * * * *